United States Patent
Elomari

(10) Patent No.: US 9,890,049 B2
(45) Date of Patent: Feb. 13, 2018

(54) MOLECULAR SIEVE SSZ-106, ITS SYNTHESIS AND USE

(71) Applicant: Chevron U.S.A. Inc., San Ramon, CA (US)

(72) Inventor: Saleh Ali Elomari, Fairfield, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 209 days.

(21) Appl. No.: 15/060,753

(22) Filed: Mar. 4, 2016

(65) Prior Publication Data

US 2017/0253491 A1    Sep. 7, 2017

(51) Int. Cl.
| | | |
|---|---|---|
| *C01B 39/48* | (2006.01) | |
| *B01J 20/18* | (2006.01) | |
| *B01J 29/70* | (2006.01) | |
| *B01D 53/94* | (2006.01) | |
| *C07D 403/08* | (2006.01) | |

(52) U.S. Cl.
CPC .......... *C01B 39/48* (2013.01); *B01D 53/9418* (2013.01); *B01D 53/9486* (2013.01); *B01J 20/18* (2013.01); *B01J 29/70* (2013.01); *C07D 403/08* (2013.01); *B01D 2255/50* (2013.01); *C01P 2002/72* (2013.01); *C01P 2002/74* (2013.01)

(58) Field of Classification Search
CPC . C01B 39/48; B01J 20/18; B01J 29/70; C01P 2002/72; C01P 2002/74
See application file for complete search history.

(56) References Cited

U.S. PATENT DOCUMENTS

| | | |
|---|---|---|
| 3,308,069 A | 3/1967 | Wadlinger et al. |
| 6,733,742 B1 | 5/2004 | Elomari |
| 6,776,973 B2 | 8/2004 | Elomari |
| 6,827,843 B2 | 12/2004 | Elomari |
| 2010/0121122 A1 | 5/2010 | Zones et al. |
| 2017/0253491 A1* | 9/2017 | Elomari ............ B01D 53/9418 |

FOREIGN PATENT DOCUMENTS

WO    2007001934    1/2007

OTHER PUBLICATIONS

Zhao et al, Characteristics of the synthetic heulandite-clinoptilolite family of zeolites, Microporous and Mesoporous Materials (21) (1998) 371-379.*

Lu et al, "Co-templated synthesis of polymorph-A enriched zeolite beta", Microporous and Mesoporous Materials 226, (2016) 19-27.*

J.M. Newsam, M.M.J. Treacy, W.T. Koetsier, and C.B. De Gruyter "Structural Characterization of Zeolite Beta" Proc. R. Soc. Lond. A 1988, 420, 375-405.

J.B. Higgins, R.B. Lapierre, J.L. Schlenker, A.C.Rohrman, J.D. Wood, G.T. Kerr, and W.J. Rohrbaugh "The Framework Topology of Zeolite Beta" Zeolites 1988, 8, 446-452.

(Continued)

*Primary Examiner* — David M Brunsman
(74) *Attorney, Agent, or Firm* — Terrence M. Flaherty

(57) ABSTRACT

Disclosed herein is a new crystalline molecular sieve designated SSZ-106, its synthesis in the presence of a structure directing agent comprising 2,3-bis(N-methylpyrrolidin-1-ylmethyl)bicyclo[2.2.1]heptane dication, and its use as an adsorbent and a catalyst.

12 Claims, 3 Drawing Sheets

(56) References Cited

OTHER PUBLICATIONS

J.B. Higgins, R.B. Lapierre, J.L. Schlenker, A.C.Rohrman, J.D. Wood, G.T. Kerr, and W.J. Rohrbaugh "The Framework Topology of Zeolite Beta—A Correction" Zeolites 1989, 9, 358.

M.A. Camblor and J. Perez-Pariente "Crystallization of Zeolite Beta: Effect of Na and K Ions" Zeolites 1991, 11, 202-210.

A. Corma, M.T. Navarro, F. Rey, J. Rius, and S. Valencia "Pure Polymorph C of Zeolite Beta Synthesized by Using Framework Isomorphous Substitution as a Structure-Directing Mechanism" Angew. Chem. Int. Ed. 2001, 40, 2277-2280.

A.W. Burton, S. Elomari, I. Chan, A. Pradhan, and C. Kibby "Structure and Synthesis of SSZ-63: Toward an Ordered Form of Zeolite Beta" J. Phys. Chem. B, 2005, 109, 20266-20275.

A. Corma, M. Moliner, A. Cantin, M.J. Diaz-Cabanas, J.L. Jorda, D. Zhang, J. Sun, K. Jansson, S. Hovmoller, and X. Zou "Synthesis and Structure of Polymorph B of Zeolite Beta" Chem. Mater. 2008, 20, 3218-3223.

International Search Report, International Appl. No. PCT/US2017/014710, dated Apr. 6, 2017.

M.A. Camblor and J. Perez-Pariente "Crystallization of zeolite beta: Effect of Na and K ions" Zeolites, 1991, 11, 202-210.

\* cited by examiner

MOLECULAR SIEVE SSZ-106, ITS SYNTHESIS AND USE

TECHNICAL FIELD

This disclosure relates to a new crystalline molecular sieve designated SSZ-106, its synthesis and its use as an adsorbent and as a catalyst.

BACKGROUND

Molecular sieve materials, both natural and synthetic, have been demonstrated in the past to be useful as adsorbents and to have catalytic properties for various types of organic conversion reactions. Certain molecular sieves, such as zeolites, aluminophosphates, and mesoporous materials, are ordered, porous crystalline materials having a definite crystalline structure as determined by X-ray diffraction. Within the crystalline molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Although many different crystalline molecular sieves have been discovered, there is a continuing need for new molecular sieves with desirable properties for gas separation and drying, organic conversion reactions, and other applications. New molecular sieves may contain novel internal pore architectures, providing enhanced selectivities in these processes.

According to the present disclosure, a new molecular sieve structure, designated SSZ-106 and having a unique X-ray diffraction pattern, has now been synthesized using 2,3-bis(N-methylpyrrolidin-1-ylmethyl)bicyclo[2.2.1]heptane dications as a structure directing agent.

SUMMARY

In one aspect, there is provided a molecular sieve having, in its calcined form, an X-ray diffraction pattern including the peaks listed in Table 2 below.

The molecular sieve, in its calcined form, has a chemical composition comprising the molar relationship:

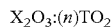

wherein n is at least 10; X is a trivalent element (e.g., one or more of B, Al, Ga, and Fe, especially Al); and T is a tetravalent element (e.g., one or more of Si, Ge, Sn, and Ti, especially Si).

In one aspect, there is provided a molecular sieve having, in its as-synthesized form, an X-ray diffraction pattern including the peaks listed in Table 3 below.

The molecular sieve has, in its as-synthesized and anhydrous form, a composition comprising the following molar relationship:

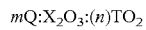

wherein 0<m≤0.2; Q comprises 2,3-bis(N-methylpyrrolidin-1-ylmethyl)bicyclo[2.2.1]heptane dications; X is a trivalent element (e.g., one or more of B, Al, Ga, and Fe, especially Al); and T is a tetravalent element (e.g., one or more of Si, Ge, Sn, and Ti, especially Si).

In one aspect, there is provided a method of preparing the molecular sieve disclosed herein, the method comprising (a) preparing a reaction mixture containing (1) at least one source of an oxide of a tetravalent element; (2) at least one source of an oxide of a trivalent element; (3) at least one source of a Group 1 or 2 metal; (4) hydroxide ions; (5) a structure directing agent comprising 2,3-bis(N-methylpyrrolidin-1-ylmethyl)bicyclo[2.2.1]heptane dication; and (6) water; and (b) subjecting the reaction mixture to crystallization conditions sufficient to form crystals of the molecular sieve.

In one aspect, there is provided a process for reducing cold start hydrocarbon emissions from a vehicle engine, the process comprising: (a) providing a hydrocarbon trap positioned in an exhaust passage of a vehicle, wherein the hydrocarbon trap comprises the molecular sieve disclosed herein; and (b) passing an exhaust gas stream comprising hydrocarbons through the hydrocarbon trap, wherein the hydrocarbon trap adsorbs at least a portion of the hydrocarbons in the exhaust gas stream at a temperature between −40° C. and 200° C.

In one aspect, there is provided a process for converting a feedstock comprising an organic compound to a conversion product which comprises the step of contacting the feedstock with a catalyst at organic compound conversion conditions, the catalyst comprising an active form of the molecular sieve described herein.

In one aspect, there is provided a process for selectively reducing nitrogen oxides ($NO_x$), the process comprising contacting a gas stream containing $NO_x$ with a catalyst comprising an active form of the molecular sieve described herein.

In one aspect, there is provided an organic nitrogen compound comprising a dication having the following structure (1):

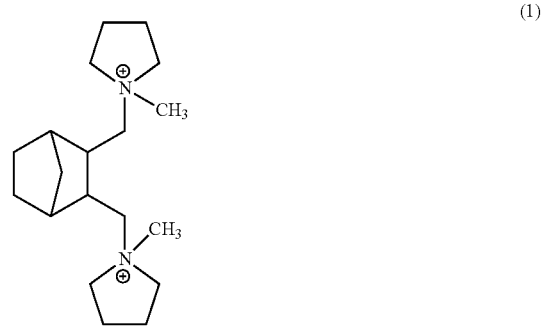 [SMILES: C[N+]1(CC2C3CCC(C3)C2C[N+]2(C)CCCC2)CCCC1]

DETAILED DESCRIPTION

Introduction

Figure 1:
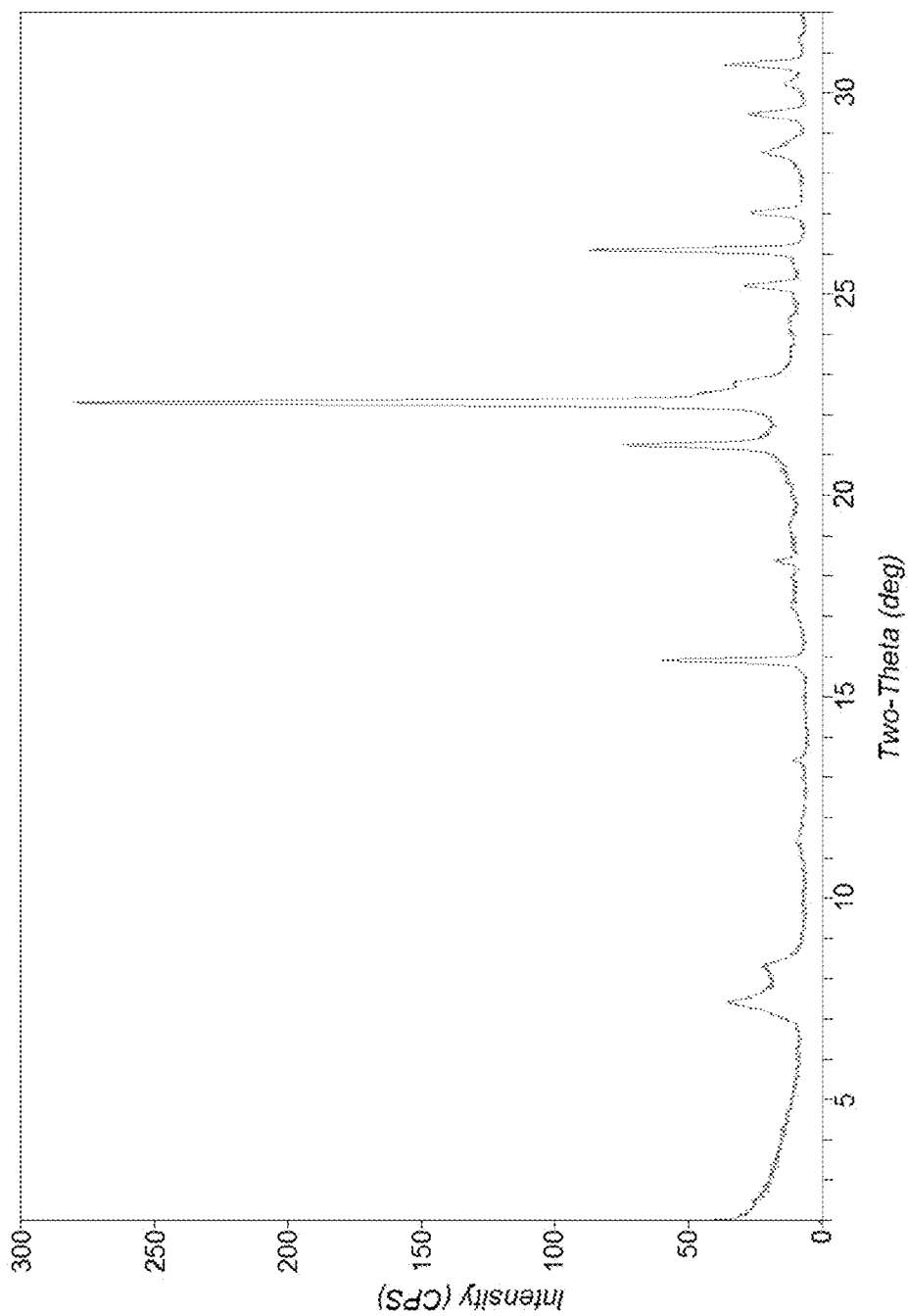
FIG. 1 shows the powder X-ray diffraction (XRD) pattern of the as-synthesized molecular sieve of Example 2.

Described herein is a novel crystalline molecular sieve, which is designated SSZ-106, its synthesis in the presence of a structure directing agent comprising 2,3-bis(N-methylpyrrolidin-1-ylmethyl)bicyclo[2.2.1]heptane dication, and its use as an adsorbent and a catalyst.

While not wishing to be bound by any theory, it is believed that SSZ-106 is structurally related to zeolite beta. Zeolite beta has a three-dimensional 12-membered-ring pore/channel system. The structure of zeolite beta has been characterized to be a highly faulted intergrowth of polymorphs, of which polymorph type A and polymorph type B are the dominant ones. The structure of zeolite beta is described in the publications by J. B. Higgins et al. (*Zeolites* 1988, 8, 446-452) and J. M. Newsam et al. (*Proc. R. Soc. Lond. A* 1988, 420, 375-405).

Reaction Mixture

In general, molecular sieve SSZ-106 is prepared by: (a) preparing a reaction mixture containing (1) at least one source of an oxide of a tetravalent element (T); (2) at least one source of an oxide of a trivalent element (X); (3) at least one source of a Group 1 or 2 metal (M); (4) hydroxide ions; (5) a structure directing agent (Q) comprising 2,3-bis(N-methylpyrrolidin-1-ylmethyl)bicyclo[2.2.1]heptane dication; and (6) water; and (b) subjecting the reaction mixture to crystallization conditions sufficient to form crystals of the molecular sieve.

The composition of the reaction mixture from which the molecular sieve is formed, in terms of mole ratios, is identified in Table 1 below:

TABLE 1

| Reactants | Useful | Exemplary |
|---|---|---|
| TO$_2$/X$_2$O$_3$ | ≥10 | 10 to 100 |
| M/TO$_2$ | 0.10 to 1.00 | 0.20 to 0.80 |
| Q/TO$_2$ | 0.05 to 0.50 | 0.15 to 0.50 |
| OH/TO$_2$ | 0.10 to 1.00 | 0.20 to 0.80 |
| H$_2$O/TO$_2$ | 15 to 100 | 15 to 50 | wherein compositional variables T, X, M and Q are as described herein above.

The tetravalent element T may be one or more of silicon (Si), germanium (Ge), tin (Sn), and titanium (Ti). Suitable sources of the tetravalent element T depend on the element T selected. Where T is Si, sources useful herein for silicon oxide include fumed silica, precipitated silicates, silica hydrogel, silicic acid, colloidal silica, tetra-alkyl orthosilicates (e.g., tetraethyl orthosilicate), and silica hydroxides.

The trivalent element X may be one or more of boron (B), aluminum (Al), gallium (Ga), and iron (Fe). Suitable sources of the trivalent element X depend on the element X selected. Where X is Al, sources useful herein for aluminum oxide include aluminates, alumina, and aluminum compounds (e.g., aluminum chloride, aluminum hydroxide, and aluminum sulfate), kaolin clays, and other zeolites (e.g., zeolite Y).

Suitable sources of Group 1 or 2 metal (M) include metal oxide, metal hydroxide, metal chloride, metal fluoride, metal sulfate, metal nitrate, and metal aluminate. As used herein, the numbering scheme for the Periodic Table Groups is as disclosed in *Chem. Eng. News*, 63(5), 26-27 (1985).

The structure directing agent (Q) comprises 2,3-bis(N-methylpyrrolidin-1-ylmethyl)bicyclo[2.2.1]heptane dication which has the following structure (1):

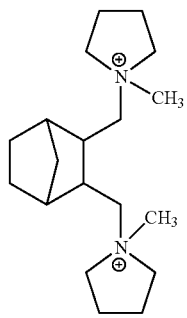

(1)

The cationic structure directing agent is associated with anions which may be any anion that is not detrimental to the formation of the molecular sieve. Representative anions include elements from Group 17 of the Periodic Table (e.g., fluoride, chloride, bromide and iodide), hydroxide, sulfate, tetrafluoroboroate, acetate, carboxylate, and the like.

Optionally, the reaction mixture may also include seeds of a molecular sieve material, such as SSZ-106 crystals from a previous synthesis, in an amount of from 0.1 to 10 wt. % (e.g., from 0.5 to 5 wt. %) of the reaction mixture.

For each embodiment described herein, the molecular sieve reaction mixture can be supplied by more than one source. Also, two or more reaction components can be provided by one source.

The reaction mixture can be prepared either batch wise or continuously. Crystal size, morphology and crystallization time of the molecular sieve described herein can vary with the nature of the reaction mixture and the crystallization conditions.

Crystallization and Post-Synthesis Treatment

Crystallization of the molecular sieve disclosed herein can be carried out under either static, tumbled or stirred conditions in a suitable reactor vessel, such as for example polypropylene jars or Teflon-lined or stainless steel autoclaves, at a temperature of from 125° C. to 200° C. (e.g., from 130° C. to 160° C.) for a time sufficient for crystallization to occur at the temperature used, e.g., from 1 day to 28 days.

Once the molecular sieve crystals have formed, the solid product is separated from the reaction mixture by standard mechanical separation techniques such as centrifugation or filtration. The crystals are water-washed and then dried to obtain the as-synthesized molecular sieve crystals. The drying step is typically performed at a temperature of less than 200° C.

As a result of the crystallization process, the recovered crystalline molecular sieve product contains within its pore structure at least a portion of the structure directing agent used in the synthesis.

To the extent desired and depending on the X$_2$O$_3$/TO$_2$ mole ratio of the molecular sieve, any cations in the as-synthesized molecular sieve can be replaced in accordance with techniques well known in the art by ion exchange with other cations. Illustrative examples of suitable replacing cations include metal ions, hydrogen ions, hydrogen precursor, e.g., ammonium ions and mixtures thereof. Particularly preferred cations are those which tailor the catalytic activity for certain organic conversion reactions. These include hydrogen, rare earth metals and metals of Groups 2 to 12 of the Periodic Table of the Elements. As used herein, the term "as-synthesized" refers to the molecular sieve in its form after crystallization, prior to removal of the SDA cation.

The organic structure directing agent is typically at least partially removed from the molecular sieve by calcination before use. Calcination consists essentially of heating the molecular sieve comprising the structure directing agent at a temperature of from 200° C. to 800° C. for an appropriate period of time in the presence of an oxygen-containing gas. The organic structure directing agent can also be removed by photolysis techniques as described in U.S. Pat. No. 6,960,327.

Characterization of the Molecular Sieve

The novel molecular sieve structure SSZ-106 is characterized by a distinctive X-ray diffraction pattern which, in the calcined form of the molecular sieve, includes at least the peaks set forth in Table 2 below and which, in the as-synthesized form of the molecular sieve, includes at least the peaks set forth in Table 3 below.

TABLE 2

Characteristic Peaks for Calcined SSZ-106

| 2-Theta[a] | d-spacing (nm) | Relative Intensity[b] |
| --- | --- | --- |
| 7.48 | 1.182 | S |
| 8.32 | 1.063 | W |
| 13.44 | 0.658 | W |
| 16.01 | 0.553 | M |
| 18.52 | 0.479 | W |
| 21.37 | 0.416 | W |
| 22.40 | 0.397 | VS |
| 22.90 | 0.388 | M |
| 24.56 | 0.362 | W |
| 25.30 | 0.352 | W |
| 26.26 | 0.339 | M |
| 27.05 | 0.329 | W |
| 28.64 | 0.311 | W |
| 29.55 | 0.302 | W |
| 30.36 | 0.294 | W |
| 30.90 | 0.289 | W |
| 33.33 | 0.269 | W |
| 36.24 | 0.248 | W |

[a] ±0.20
[b] The powder XRD patterns provided are based on a relative intensity scale in which the strongest line in the X-ray diffraction pattern is assigned a value of 100: W = weak (>0 to ≤20); M = medium (>20 to ≤40); S = strong (>40 to ≤60); VS = very strong (>60 to ≤100).

TABLE 3

Characteristic Peaks for As-Synthesized SSZ-106

| 2-Theta[a] | d-spacing (nm) | Relative Intensity[b] |
| --- | --- | --- |
| 7.38 | 1.196 | W |
| 13.41 | 0.660 | W |
| 15.90 | 0.557 | W |
| 18.39 | 0.482 | W |
| 21.26 | 0.418 | M |
| 22.31 | 0.398 | VS |
| 22.80 | 0.390 | M |
| 25.20 | 0.353 | W |
| 26.09 | 0.341 | M |
| 27.01 | 0.330 | W |
| 28.53 | 0.313 | W |
| 29.47 | 0.303 | W |
| 30.19 | 0.296 | W |
| 30.70 | 0.291 | W |
| 33.18 | 0.270 | W |
| 33.45 | 0.268 | W |
| 36.00 | 0.250 | W |
| 37.24 | 0.241 | W |

[a] ±0.20
[b] The powder XRD patterns provided are based on a relative intensity scale in which the strongest line in the X-ray diffraction pattern is assigned a value of 100: W = weak (>0 to ≤20); M = medium (>20 to ≤40); S = strong (>40 to ≤60); VS = very strong (>60 to ≤100).

The powder X-ray diffraction patterns presented herein were collected by standard techniques. The radiation was CuK$_\alpha$ radiation. The peak heights and the positions, as a function of 2θ where θ is the Bragg angle, were read from the relative intensities of the peaks (adjusting for background), and d, the interplanar spacing corresponding to the recorded lines, can be calculated.

Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation. Calcination can also cause minor shifts in the XRD pattern. Notwithstanding these minor perturbations, the basic crystal lattice structure remains unchanged.

In its calcined form, molecular sieve SSZ-106 has a chemical composition comprising the molar relationship:

$$X_2O_3:(n)TO_2$$

wherein n is at least 10 (e.g., 10 to 100, 10 to 50, 10 to 25, 15 to 100, or 15 to 50); X is a trivalent element (e.g., one or more of B, Al, Ga, and Fe, especially Al); and T is a tetravalent element (e.g., one or more of Si, Ge, Sn, and Ti, especially Si).

In its as-synthesized and anhydrous form, molecular sieve SSZ-104 has a chemical composition comprising the molar relationship:

$$mQ:X_2O_3:(n)TO_2$$

wherein 0<m≤0.2; n is at least 10 (e.g., 10 to 100, 10 to 50, 10 to 25, 15 to 100, or 15 to 50); X is a trivalent element (e.g., one or more of B, Al, Ga, and Fe, especially Al); T is a tetravalent element (e.g., one or more of Si, Ge, Sn, and Ti, especially Si); and Q comprises 2,3-bis(N-methylpyrrolidin-1-ylmethyl)bicyclo[2.2.1]heptane dication.

It should be noted that the as-synthesized form of the molecular sieve disclosed herein may have molar ratios different from the molar ratios of reactants of the reaction mixture used to prepare the as-synthesized form. This result may occur due to incomplete incorporation of 100% of the reactants of the reaction mixture into the crystals formed (from the reaction mixture).

Processes Using Molecular Sieve SSZ-106

Molecular sieve SSZ-106 can be used as an adsorbent or as a catalyst to catalyze a wide variety of chemical conversion processes including many of present commercial/industrial importance.

Hydrocarbon Trap

Molecular sieve SSZ-106 may be used as a hydrocarbon trap (e.g., a pre-catalytic converter adsorbent) for reducing cold-start hydrocarbon emissions in motor vehicles.

In recent years, considerable efforts have been made to reduce the level of hydrocarbon (HC) emissions from motor vehicle engines. Conventional exhaust treatment catalysts such as three-way catalysts achieve conversion of hydrocarbons to water and help prevent the exit of unburnt or partially burnt hydrocarbon emissions from a vehicle. However, hydrocarbon emissions are high during cold starting of the engine before the latent heat of the exhaust gas heats the catalyst and allows it to become active (i.e., before the catalyst has reached its "light-off" temperature).

Hydrocarbon traps have been developed for reducing emissions during cold-start by trapping/adsorbing hydrocarbon (HC) emissions at low temperatures and releasing/desorbing them from the trap at sufficiently elevated temperatures for oxidation over a catalyst, such as a three-way catalyst. The HC traps are positioned in the exhaust gas stream of a vehicle. Currently, molecular sieves have been the most widely used adsorption materials for hydrocarbon traps. The molecular sieves are typically combined with a three-way catalyst in the form of a washcoat which is supported on a monolithic substrate.

As exhaust gases pass through the exhaust system of a vehicle, the hydrocarbon trap provides improved adsorption of hydrocarbon emissions and retains the hydrocarbons until the exhaust gases heat the trap to a sufficient temperature for catalytic conversion (i.e., about 200° C. to 400° C.) at which time the hydrocarbons are desorbed and are oxidized by the three-way catalyst in the trap. The trap is positioned in the exhaust gas system of a vehicle such that gases pass through the trap (e.g., at a gas space velocity of about 30,000 $h^{-1}$) and the trap adsorbs and retains at least a portion (e.g., about 50 to 90 wt. %) of the hydrocarbons in the exhaust gas at a temperature between about −40° C. and 200° C.

The hydrocarbon adsorbent disclosed herein is a composition which comprises molecular sieve SSZ-106 and a binder also referred to as a washcoat binder.

Suitable washcoat binders sols of alumina, silica, ceria and zirconia; inorganic and organic salts and hydrolysis products thereof of aluminum, silicon, cerium and zirconium such as nitrates, nitrites, halides, sulfates and acetates; hydroxides of aluminum, silicon, cerium, zirconium, and combinations of all of the above components. Also useful as binders are organic silicates which are hydrolyzable to silica including tetraethyl orthosilicates.

The adsorbent material may be deposited onto a solid monolithic carrier by methods known in the art. It is usually most convenient to apply the adsorbent as a thin film or coating deposited on an inert carrier material which provides the structural support for the adsorbent. The inert carrier material can be any refractory material such as ceramic or metallic materials. Alternatively, the adsorbent may be provided in the form of pellets or beads disposed in a flow-through canister to provide an adsorbent bed through which exhaust gases flow. The adsorbent material may also be extruded or otherwise fabricated into monolithic form and disposed within the exhaust gas stream.

A three-way catalyst material may be coated over the molecular sieve washcoat at about 30 to 70% by weight solids to a loading of 1 to 2 g/in$^3$. Suitable three-way catalyst metals include platinum, palladium, rhodium, and combinations thereof.

An oxygen storage capacity (OSC) material may also be included in the molecular sieve washcoat slurry in an amount of about 10% by weight solids or less (e.g., 5% by weight solids or less). Suitable OSC materials include ceria-zirconia (CZO) and ceria-praesodymium, or base metals such as NiO—CuO and MnO$_2$.

In embodiments where the three-way catalyst (TWC) material is coated over the molecular sieve, the TWC material may be applied by washcoating. For example, the three-way catalyst may be coated on the surface of the molecular sieve coated monolith substrate by conventional techniques known in the art. The use of a separate TWC washcoat layer over the molecular sieve layer provides a barrier between the platinum group metal in the TWC and the molecular sieve while providing direct contact between the platinum group metal and OSC material.

Organic Compound Conversion

Molecular sieve SSZ-106 can be used as a catalyst or catalyst support in various organic compound conversion processes.

Specific examples of organic compound conversion processes include hydrocarbon conversion reactions, such as:

(a) alkylation of aromatics with short chain ($C_2$-$C_6$) olefins, e.g., alkylation of ethylene or propylene with benzene to produce ethylbenzene or cumene respectively, in the gas or liquid phase, with reaction conditions optionally including one or more of a temperature from 10° C. to 250° C., a pressure from 0 to 500 psig (3.5 MPa), a total weight hourly space velocity (WHSV) from 0.5 to 100 $h^{-1}$, and an aromatic/olefin mole ratio from 0.1 to 50;

(b) alkylation of aromatics with long chain ($C_{10}$-$C_{20}$) olefins, in the gas or liquid phase, with reaction conditions optionally including one or more of a temperature from 250° C. to 500° C., a pressure from 0 to 500 psig (3.5 MPa), a total WHSV from 0.5 to 50 $h^{-1}$, and an aromatic/olefin mole ratio from 1 to 50;

(c) transalkylation of aromatics, in gas or liquid phase, e.g., transalkylation of polyethylbenzenes and/or polyisopropylbenzenes with benzene to produce ethylbenzene and/or cumene respectively, with reaction conditions optionally including one or more of a temperature from 100° C. to 500° C., a pressure from 1 to 500 psig (7 kPa to 3.5 MPa), and a WHSV from 1 to 10,000 $h^{-1}$;

(d) disproportionation of alkylaromatics, e.g., disproportionation of toluene to produce xylenes, with reaction conditions optionally including one or more of a temperature from 200° C. to 760° C., a pressure from 1 to 60 atm (0.1 to 5.9 MPa), a WHSV from 0.1 to 20 $h^{-1}$, and a hydrogen/hydrocarbon mole ratio from 0 (no added hydrogen) to 50;

(e) dealkylation of alkylaromatics, e.g., de-ethylation of ethylbenzene, with reaction conditions optionally including one or more of a temperature from 200° C. to 760° C., a pressure from 1 to 60 atm (0.1 to 5.9 MPa), a WHSV from 0.1 to 20 $h^{-1}$, and a hydrogen to hydrocarbon mole ratio from 0 (no added hydrogen) to 50;

(f) isomerization of alkylaromatics, such as xylenes, with reaction conditions optionally including one or more of a temperature from 200° C. to 540° C., a pressure from 100 kPa to 7 MPa, a WHSV from 0.1 to 50 $h^{-1}$, and a hydrogen/hydrocarbon mole ratio from 0 (no added hydrogen) to 10;

(g) reaction of paraffins with aromatics, e.g., to form alkylaromatics and light gases, with reaction conditions optionally including one or more of a temperature from 260° C. to 375° C., a pressure from 0 to 1000 psig (6.9 MPa), a WHSV from 0.5 to 10 $h^{-1}$, and a hydrogen/hydrocarbon mole ratio from 0 (no added hydrogen) to 10;

(h) paraffin isomerization to provide branched paraffins with reaction conditions optionally including one or more of a temperature from 200° C. to 315° C., a pressure from 100 to 1000 psig (0.69 to 6.9 MPa), a WHSV from 0.5 to 10 $h^{-1}$, and a hydrogen to hydrocarbon mole ratio from 0.5 to 10;

(i) alkylation of iso-paraffins, such as isobutane, with olefins, with reaction conditions optionally including one or more of a temperature from −20° C. to 350° C., a pressure from 0 to 700 psig (4.9 MPa), and a total olefin WHSV from 0.02 to 10 $h^{-1}$;

(j) dewaxing of paraffinic feeds or other hydrocarbonaceous feedstocks, such as petroleum feedstocks; with reaction conditions optionally including one or more of a temperature from 200° C. to 450° C., a pressure from 0 psig to 1000 psig (6.9 MPa), a WHSV from 0.2 to 10 $h^{-1}$, and a hydrogen/hydrocarbon mole ratio from 0.5 to 10;

(k) cracking of hydrocarbons with reaction conditions optionally including one or more of a temperature from 300° C. to 700° C., a pressure from 0.1 atm to 30 atm (10 kPa to 3 MPa), and a WHSV from 0.1 to 20 $h^{-1}$; and (l) isomerization of olefins with reaction conditions optionally including one or more of a temperature from 250° C. to 750° C., an olefin partial pressure from 30 to 300 kPa, and a WHSV from 0.5 to 500 h$^{-1}$.

As in the case of many catalysts, it may be desirable to incorporate molecular sieve SSZ-106 with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring, or in the form of gelatinous precipitates or gels, including mixtures of silica and metal oxides. Use of a material in conjunction with molecular sieve SSZ-106, i.e., combined therewith or present during synthesis of the new molecular sieve, which is active, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. These materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with molecular sieve SSZ-106 include the montmorillonite and kaolin family, which families include the sub-bentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with SSZ-106 also include inorganic oxides, such as silica, zirconia, titania, magnesia, beryllia, alumina, and mixtures thereof.

In addition to the foregoing materials, molecular sieve SSZ-106 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of molecular sieve SSZ-106 and inorganic oxide matrix may vary widely, with the SSZ-106 content ranging from 1 to 90 wt. %, and more usually, in the range of 2 to 80 wt. % of the composite.

Reduction of Nitrogen Oxides

Molecular sieve SSZ-106 may be used in a catalytic process involving the conversion of at least one compound comprising at least one nitrogen-oxygen bond. Particularly preferred are processes wherein molecular sieve SSZ-106 is used as a catalyst and/or catalyst support in a selective catalytic reduction (SCR) process. Selective catalytic reduction refers to the catalytic process of reducing nitrogen oxides ($NO_x$) in a gas stream to dinitrogen ($N_2$) using a nitrogenous reductant.

The term "nitrogen oxides" ($NO_x$), as used in the context of the present disclosure, designates the oxides of nitrogen, especially nitrogen monoxide (NO), nitrogen dioxide ($NO_2$), nitrogen peroxide ($NO_3$), dinitrogen oxide ($N_2O$), dinitrogen trioxide ($N_2O_3$), dinitrogen tetroxide ($N_2O_4$), and dinitrogen pentoxide ($N_2O_5$).

The nitrogen oxides which are reduced using a catalyst containing molecular sieve SSZ-106 may be obtained by any process (e.g., as a waste gas stream). Combustion of any fossil fuel generates some level of $NO_x$ due to high temperatures and the availability of oxygen and nitrogen from both the air and fuel. In one embodiment, the gas stream containing $NO_x$ is an exhaust gas from an internal combustion engine.

Therefore, the present disclosure also relates to a process for selectively reducing nitrogen oxides by contacting a gas stream containing $NO_x$ with a catalyst containing molecular sieve SSZ-106 under suitable reducing conditions. The contacting of the gas stream with the catalyst comprising molecular sieve SSZ-106 takes place at an elevated temperature compared to ambient temperature, more preferably at a temperature in the range of anywhere from 150° C. to 700° C. (e.g., from 200° C. to 600° C.). The gas stream preferably also contains one or more reducing agents (e.g., urea and/or ammonia) which are active in the SCR process when simultaneously contacted with both the catalyst and $NO_x$ contained in the gas stream.

For the selective reduction of nitrogen oxides, molecular sieve SSZ-106 may be used in the form of a molded catalyst, preferably as a molded catalyst wherein molecular sieve SSZ-106 is deposited on a suitable refractory carrier, such as on a "honeycomb" carrier.

The catalyst typically comprises one or more transition metals (e.g., one or more of Cr, Mo, Mn, Re, Fe, Ru, Co, Rh, Ir, Ni, Pd, Pt, Cu, and Zn) supported on the molecular sieve in an amount of from 0.1 to 10 wt %, based on the total weight of the molecular sieve.

The reduction of nitrogen oxides may be carried out in the presence of oxygen or in the absence of oxygen.

EXAMPLES

The following illustrative examples are intended to be non-limiting.

Example 1

Synthesis of 2,3-bis(N-methylpyrrolidin-1-ylmethyl) bicyclo[2.2.1]heptane dihydroxide In a 3-neck 500 mL round bottom reaction flask equipped with an overhead stirrer and reflux condenser, 40 g (0.4 mol) of triethylamine and 29 g (0.4 mol) of pyrrolidine were dissolved in 320 mL of cyclohexane. The mixture was cooled to 0° C. using a water-ice bath. Then, a solution of 35 g (0.16 mol) of bicyclo[2.2.1]hept-5-ene-2,3-dicarbonyl chloride in 50 mL of cyclohexane was added dropwise via an addition (dropping) funnel while stirring over a 30 minute period. Once all the dichloride was added, the reaction mixture was left to stir and warm up gradually to room temperature. The reaction mixture was then left to stir at room temperature overnight and then was heated to reflux for 4 hours. The resulting reaction solution, a solid phase and a liquid phase, was left to cool down and then, 500 mL of ethyl acetate and 500 mL of water were added to the reaction mixture. The aqueous phase was removed and the organic phase was washed 2×500 mL of water and once with 500 mL of brine. The organic phase was dried over anhydrous magnesium sulfate, filtered and concentrated on a rotary evaporator at reduced pressure (15 torr) and at 70° C. The reaction afforded the desired di-amide product, bicyclo[2.2.1]hept-5-ene-2,3-diylbis(pyrrolidine-1-yl)methanone as a tan solid material in 96.4% yield (44.5 g). The product was confirmed by NMR and IR spectroscopy.

Bicyclo[2.2.1]hept-5-ene-2,3-diylbis(pyrrolidine-1-yl)methanone was hydrogenated to the corresponding bicyclo[2.2.1]heptane-2,3-diylbis(pyrrolidine-1-yl)methanone by dissolving the product obtained in the previous reaction (44 g) in 250 mL of ethanol in a hydrogenation glass bottle. Then, 3 g of 10% Pd on activated carbon was added and the hydrogenation bottle was affixed to a Parr hydrogenation apparatus at a hydrogen pressure of 60 psig. The reaction was left to gently rock overnight. The reaction mixture was then filtered over a thin bed of CELITE® diatomaceous earth in a frit glass funnel. The filtrate was concentrated on a rotary evaporator at reduced pressure (13 torr) and at 75° C. The hydrogenation reaction afforded the desired product, bicyclo[2.2.1]heptane-2,3-diylbis(pyrrolidine-1-yl)methanone, in 97% yield (43.8 g). The product was confirmed by NMR and IR spectroscopy.

A 3-neck 1-liter reaction flask equipped with reflux condenser and an overhead stirrer was charged with 250 mL anhydrous tetrahydrofuran (THF). Then, 18 g (0.47 mol) of lithium aluminum hydride (95% purity) was suspended in the THF. The suspension was cooled down to 0° C. in a water-ice bath. Then, bicyclo[2.2.1]heptane-2,3-diylbis(pyrrolidine-1-yl)methanone (42.5 g, 0.15 mol) was dissolved in 250 mL of THF and added dropwise to the LiAlH$_4$-THF suspension via a dropping funnel over 30 minutes. Following addition, the water-ice bath was removed and the reaction mixture was heated at reflux for 4 hours. The reaction mixture was then left to stir at room temperature overnight. The reaction mixture was cooled down to 0° C. (water-ice bath). The reaction was worked up by drop-wise addition of a sodium hydroxide solution (120 mL of 15 wt. % aqueous solution) with vigorous stirring over a 45 minute period. The resulting biphasic mixture (a colorless liquid and a white precipitate) was filtered. The filtrate was dried over anhydrous magnesium sulfate, filtered and concentrated on a rotary evaporator at reduced pressure (15 torr) and at 60° C. The reaction afforded the desired 2,3-bis(pyrrolidin-1-ylmethyl)bicyclo[2.2.1]heptane in 92% yield (35.7 g) as yellow oil. The product was confirmed by NMR and IR spectroscopy.

In a 250 mL round bottom reaction flask, 20 g (0.076 mol) of 2,3-bis(pyrrolidin-1-ylmethyl)bicyclo[2.2.1]heptane was dissolved in 160 mL of methanol. Then, 33 g (0.23 mol) of methyl iodide was added. The resulting mixture was heated to reflux and left to stir at reflux overnight. Then, an additional 10 g of methyl iodide was added and the reaction mixture was allowed to further stir at room temperature for 72 hours. The reaction mixture was then worked up by removing the solvent and excess methyl iodide on a rotary evaporator at reduced pressure and at 50° C. The resulting tan solids were dissolved in acetone and then recrystallized by adding diethyl ether. The resulting precipitate was filtered and dried on a rotary evaporator at reduced pressure (10 torr) and at 70° C. The reaction afforded the desired 2,3-bis(N-methylpyrrolidin-1-ylmethyl)bicyclo[2.2.1]heptane diiodide in 82% yield (24.88 g).

24 g (87.8 mmol iodide) of the diiodide salt was dissolved in 110 mL of deionized water. Then, 102 g of BIO-RAD AG® 1-X8 hydroxide-based ion exchange resins was added to the solution and the mixture was gently stirred overnight. The mixture was filtered and the filtrate was analyzed for OH ion concentration by titration of a small aliquot. The exchange reaction afforded the dihydroxide derivative in 91% yield (80 mmol OH).

Scheme A below depicts the synthesis of 2,3-bis(N-methylpyrrolidin-1-ylmethyl)bicyclo[2.2.1]heptane dihydroxide.

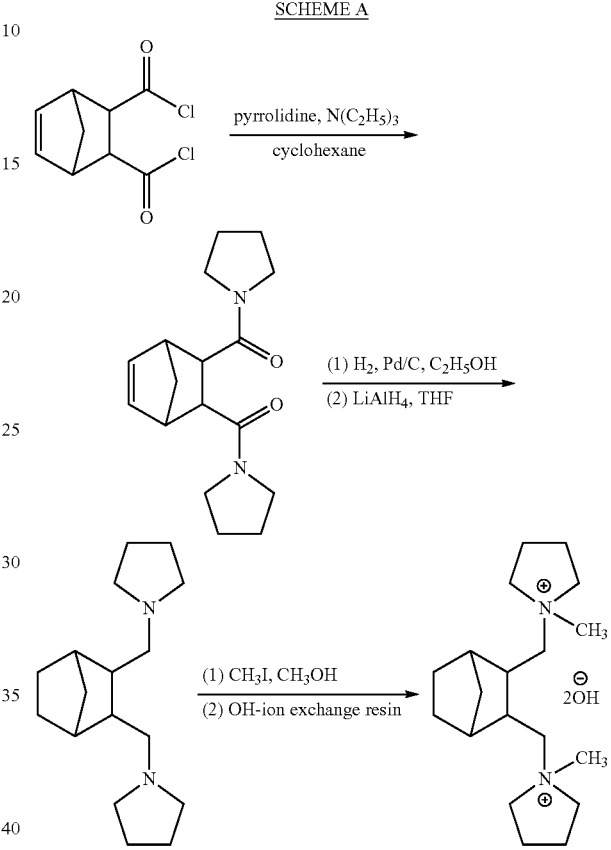

Example 2

Synthesis of Aluminosilicate SSZ-106

In a 23 cc Teflon liner, 3.4 g of SDA solution (1.01 mmol SDA; 2.02 mmol cation), 0.2 g of 1N sodium hydroxide solution (aqueous), 0.25 g of Na—Y zeolite, 2.5 g of Na-silicate solution, and 2.8 g of deionized water were mixed thoroughly until a homogenous mixture was obtained. The Teflon liner was capped and sealed in a Parr autoclave. The autoclave was affixed on a rotating spit (43 rpm) in a heated oven at 150° C. The autoclave was heated for 6 days. SEM indicated reaction completion by full crystallinity of the products. The reaction mixture (with a clear liquid layer and settled fine powdery material and a pH of >12.2-12.7) was filtered. The obtained fine solid was thoroughly rinsed with water. The product was left to dry in open air overnight and then dried in a heated oven at 125° C. for 1 hour. The reaction afforded 0.55 g of pure crystalline zeolite as indicated by SEM and powder XRD analysis.

The powder XRD pattern of the as-synthesized product is shown in FIG. 1.

Figure 2A:
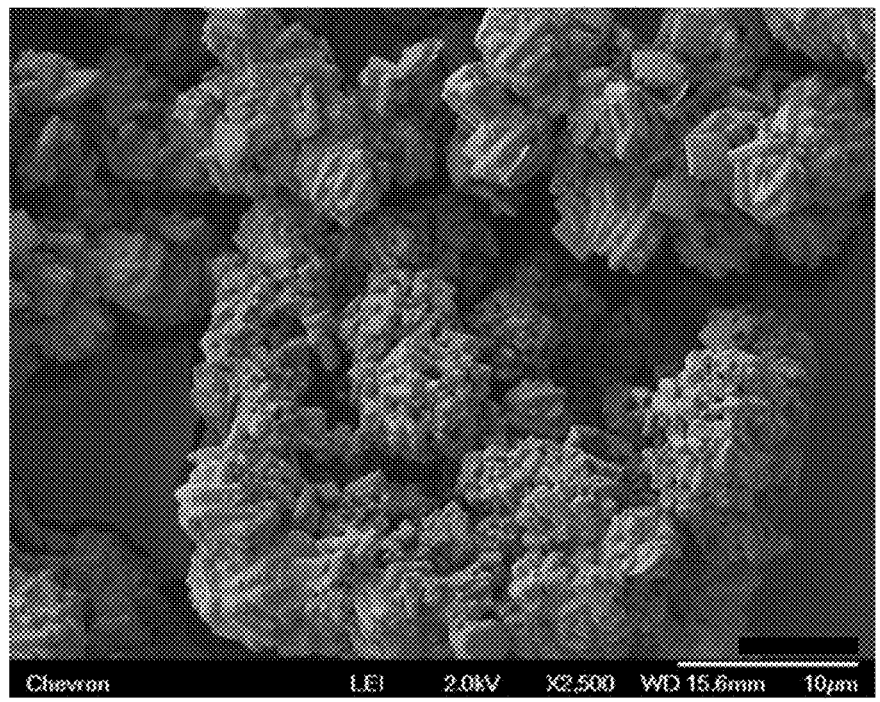
FIGS. 2(*a*) and 2(*b*) are Scanning Electron Micrograph (SEM) images of the as-synthesized molecular sieve of Example 2 at different magnifications.
Figure 2B:
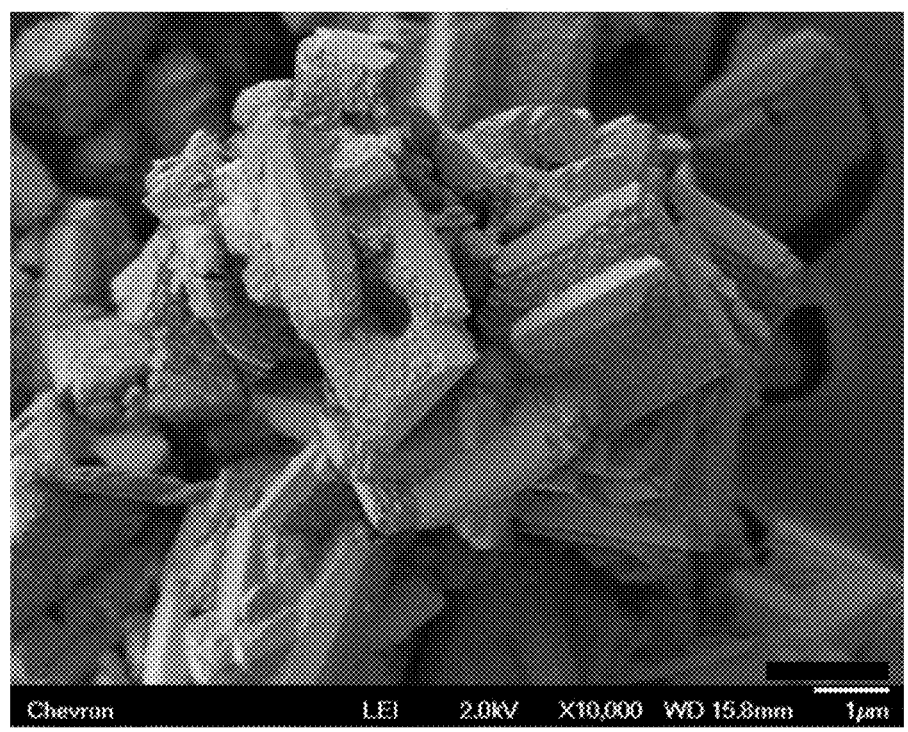

SEM images of the as-synthesized product at different magnifications are shown FIGS. 2(*a*) and 2(*b*). The SEM images indicate that the as-synthesized product has a different morphology than the spherical-shaped crystals reported for aluminosilicate zeolite beta (M. A. Camblor et al., *Zeolites* 1991, 11, 202-210).

Example 3

Synthesis of Aluminosilicate SSZ-106

In a 23 cc Teflon liner, 3.4 g of SDA solution (1.01 mmol SDA; 2.02 mmol cation), 0.2 g of 1N sodium hydroxide solution (aqueous), 0.25 g of $NH_4$—Y zeolite and 2.5 g of sodium silicate colloid, and 2.6 g of deionized water were mixed thoroughly until a homogenous mixture was obtained. The Teflon liner was capped and sealed in a Parr autoclave. The autoclave was affixed on a rotating spit (43 rpm) in a heated oven at 150° C. The autoclave was heated for 6 days. SEM indicated reaction completion by full crystallinity of the products. The reaction mixture (with a clear liquid layer and settled fine powdery material and a pH of 12.8) was filtered. The obtained fine solids were thoroughly rinsed with water. The product was left to dry in open air overnight and then was dried in a heated oven at 125° C. for 1 hour. The reaction afforded 0.51 g of pure crystalline zeolite as indicated by SEM and powder XRD analysis.

Example 4

Synthesis of Aluminosilicate SSZ-106

Example 2 was repeated except that more SDA solution was added (4.8 g rather than 3.4 g) and no NaOH was used. The reaction was completed in 6 days with final pH of 12.6. The reaction afforded 0.54 g of the same product obtained in Example 2 as indicated by SEM and powder XRD analysis.

Example 5

Calcination of SSZ-106

Figure 3:
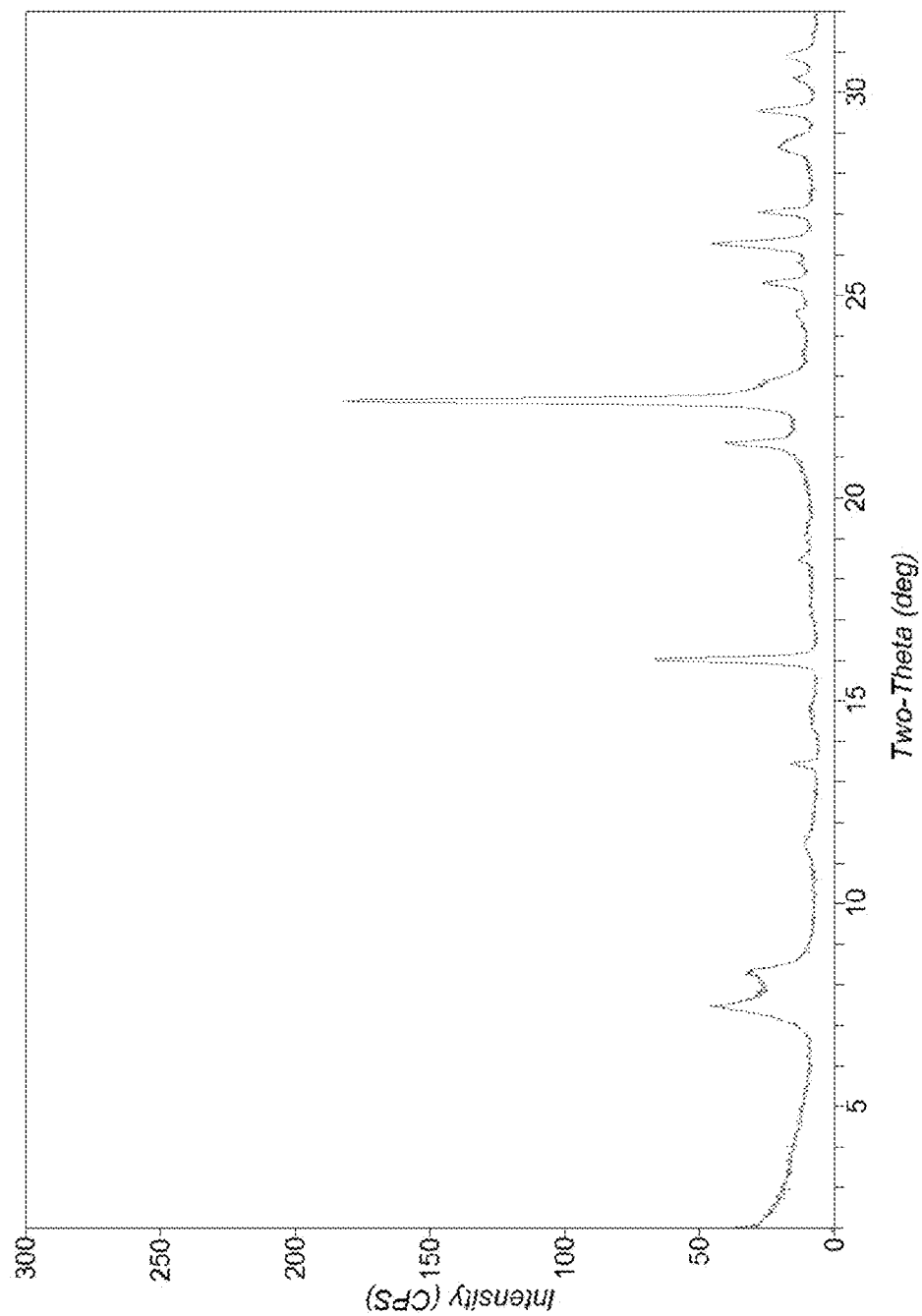
FIG. 3 shows powder XRD pattern of the calcined molecular sieve prepared in Example 5.

The as-synthesized product from Example 2 was calcined in air in a muffle furnace from room temperature to 120° C. at a rate of 1° C./minute and held at 120° C. for 2 hours. The temperature was then ramped up to 540° C. at a rate of 1° C./minute and held at 540° C. for 5 hours. The temperature was then increased at the same rate (1° C./min) to 595° C. at held at 595° C. for 5 hours. The powder XRD pattern of the calcined molecular sieve is shown in FIG. 3 and indicates that the material remains stable after calcination to remove the organic SDA.

The calcined material had a $SiO_2/Al_2O_3$ mole ratio of 16, as determined by ICP elemental analysis.

The micropore volume and external surface area of calcined SSZ-106 were then measured by nitrogen physisorption using the BET method. The measured micropore volume was 0.19 cm$^3$/g, the external surface area was 88 m$^2$/g and the BET surface area was 482 m$^2$/g.

As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

All documents cited in this application are herein incorporated by reference in their entirety to the extent such disclosure is not inconsistent with this text.

The invention claimed is:

1. A molecular sieve having, in its calcined form, an X-ray diffraction pattern including the peaks in following table:

| 2-Theta | d-spacing (nm) | Relative Intensity |
|---|---|---|
| 7.48 ± 0.20 | 1.182 | S |
| 8.32 ± 0.20 | 1.063 | W |
| 13.44 ± 0.20 | 0.658 | W |
| 16.01 ± 0.20 | 0.553 | M |
| 18.52 ± 0.20 | 0.479 | W |
| 21.37 ± 0.20 | 0.416 | W |
| 22.40 ± 0.20 | 0.397 | VS |
| 22.90 ± 0.20 | 0.388 | M |
| 24.56 ± 0.20 | 0.362 | W |
| 25.30 ± 0.20 | 0.352 | W |
| 26.26 ± 0.20 | 0.339 | M |
| 27.05 ± 0.20 | 0.329 | W |
| 28.64 ± 0.20 | 0.311 | W |
| 29.55 ± 0.20 | 0.302 | W |
| 30.36 ± 0.20 | 0.294 | W |
| 30.90 ± 0.20 | 0.289 | W |
| 33.33 ± 0.20 | 0.269 | W |
| 36.24 ± 0.20 | 0.248 | W. |

2. The molecular sieve of claim 1, and having a composition comprising the molar relationship:

$$X_2O_3{:}(n)TO_2$$

wherein n is at least 10; X is a trivalent element; and T is a tetravalent element.

3. The molecular sieve of claim 2, wherein X includes one or more of B, Al, Ga, and Fe; and T includes one or more of Si, Ge, Sn, and Ti.

4. The molecular sieve of claim 2, wherein X includes Al and T includes Si.

5. A molecular sieve having, in its as-synthesized form, an X-ray diffraction pattern including the peaks in the following table:

| 2-Theta | d-spacing (nm) | Relative Intensity |
|---|---|---|
| 7.38 ± 0.20 | 1.196 | W |
| 13.41 ± 0.20 | 0.660 | W |
| 15.90 ± 0.20 | 0.557 | W |
| 18.39 ± 0.20 | 0.482 | W |
| 21.26 ± 0.20 | 0.418 | M |
| 22.31 ± 0.20 | 0.398 | VS |
| 22.80 ± 0.20 | 0.390 | M |
| 25.20 ± 0.20 | 0.353 | W |
| 26.09 ± 0.20 | 0.341 | M |
| 27.01 ± 0.20 | 0.330 | W |
| 28.53 ± 0.20 | 0.313 | W |
| 29.47 ± 0.20 | 0.303 | W |
| 30.19 ± 0.20 | 0.296 | W |
| 30.70 ± 0.20 | 0.291 | W |
| 33.18 ± 0.20 | 0.270 | W |
| 33.45 ± 0.20 | 0.268 | W |
| 36.00 ± 0.20 | 0.250 | W |
| 37.24 ± 0.20 | 0.241 | W. |

6. The molecular sieve of claim 5, and having a composition comprising the following molar relationship:

$$mQ{:}X_2O_3{:}(n)TO_2$$

wherein:
(a) 0<m≤0.2;
(b) Q comprises 2,3-bis(N-methylpyrrolidin-1-ylmethyl) bicyclo[2.2.1]heptane dication;

(c) X is a trivalent element; and
(d) T is a tetravalent element.

7. The molecular sieve of claim 6, wherein X includes one or more of B, Al, Ga, and Fe; and T includes one or more of Si, Ge, Sn, and Ti.

8. The molecular sieve of claim 6, wherein X includes Al and T includes Si.

9. A method of preparing the molecular sieve of claim 6, comprising
(a) preparing a reaction mixture containing
  (1) at least one source of an oxide of a tetravalent element (T);
  (2) at least one source of an oxide of a trivalent element (X);
  (3) at least one source of a Group 1 or 2 metal (M);
  (4) hydroxide ions;
  (5) a structure directing agent (Q) comprising 2,3-bis(N-methylpyrrolidin-1-ylmethyl)bicyclo[2.2.1]heptane dication; and
  (6) water; and
(b) subjecting the reaction mixture to crystallization conditions sufficient to form crystals of the molecular sieve,
wherein the reaction mixture comprises, in terms of mole ratios, the following:

| | |
|---|---|
| $TO_2/X_2O_3$ | ≥10 |
| $M/TO_2$ | 0.10 to 1.00 |
| $Q/TO_2$ | 0.05 to 0.50 |
| $OH/TO_2$ | 0.10 to 1.00 |
| $H_2O/TO_2$ | 15 to 100. |

10. The method of claim 9, wherein the reaction mixture comprises, in terms of mole ratios, the following:

| | |
|---|---|
| $TO_2/X_2O_3$ | 10 to 100 |
| $M/TO_2$ | 0.20 to 0.80 |
| $Q/TO_2$ | 0.15 to 0.50 |
| $OH/TO_2$ | 0.20 to 0.80 |
| $H_2O/TO_2$ | 15 to 50. |

11. The method of claim 9, wherein X includes one or more of B, Al, Ga, and Fe; and T includes one or more of Si, Ge, Sn, and Ti.

12. The method of claim 9, wherein X includes Al and T includes Si.

* * * * *